(12) United States Patent
Miesel et al.

(10) Patent No.: US 7,513,884 B2
(45) Date of Patent: Apr. 7, 2009

(54) BRANCHING CATHETER SYSTEMS WITH DIAGNOSTIC COMPONENTS

(75) Inventors: Keith A. Miesel, St. Paul, MN (US); Justin A. Blanco, Philadelphia, PA (US)

(73) Assignee: Medtronic, Inc., Minneapolis, MN (US)

( * ) Notice: Subject to any disclaimer, the term of this patent is extended or adjusted under 35 U.S.C. 154(b) by 109 days.

(21) Appl. No.: 11/112,219

(22) Filed: Apr. 22, 2005

(65) Prior Publication Data

US 2005/0245858 A1    Nov. 3, 2005

Related U.S. Application Data

(60) Provisional application No. 60/564,473, filed on Apr. 22, 2004.

(51) Int. Cl.
*A61M 31/00* (2006.01)
(52) U.S. Cl. .................. 604/65; 604/93.01; 604/246
(58) Field of Classification Search .............. 604/65, 604/523, 533, 537, 284, 67, 93.01, 256
See application file for complete search history.

(56) References Cited

U.S. PATENT DOCUMENTS

| | | | |
|---|---|---|---|
| 3,671,979 A | 6/1972 | Moulopoulos | |
| 4,397,335 A | 8/1983 | Doblar et al. | |
| 4,411,292 A | 10/1983 | Schiller et al. | |
| 4,550,748 A | 11/1985 | Nunez | |
| 4,759,752 A | 7/1988 | Stober | |
| 4,834,704 A | 5/1989 | Reinicke | |
| 5,006,997 A | 4/1991 | Reich | |
| 5,279,544 A | 1/1994 | Gross et al. | |
| 5,342,298 A | 8/1994 | Michaels et al. | |
| 5,395,352 A | 3/1995 | Penny | |
| 5,531,684 A * | 7/1996 | Ensminger et al. | 604/288.03 |
| 5,558,640 A | 9/1996 | Pfeiler et al. | |
| 5,605,545 A | 2/1997 | Nowosielski et al. | |
| 5,746,722 A | 5/1998 | Pohndorf et al. | |

(Continued)

FOREIGN PATENT DOCUMENTS

EP    0 564 321 A    10/1993

(Continued)

*Primary Examiner*—Nicholas D Lucchesi
*Assistant Examiner*—Laura A Bouchelle
(74) *Attorney, Agent, or Firm*—Mueting, Raasch & Gebhardt, P.A.

(57) ABSTRACT

Branching catheter systems with diagnostic components for detecting and isolating fluid flow problems (e.g., leaks, occlusions, etc.) and methods for detecting and isolating fluid flow problems are disclosed. Among the fluid flow problems that may potentially be detected are leaks in the branching catheter systems (e.g., cuts, disconnected components, etc.). Another fluid flow problem that may be detected using the diagnostic systems of the present invention is the presence of occlusions or other blockages that prevent fluid flow within the catheter systems. In addition to identifying that a problem exists, the diagnostic components may preferably also be used to identify the location of the fluid flow problem as discussed herein. Connectors for use in the branching catheter systems are also disclosed. Among the diagnostic components that may be used in branching catheter systems of the present are valves to control fluid flow through the various sections of the branching catheter system, fluid flow detectors to detect flow through the one or more sections of the branching catheter system and a control system for operating the diagnostic components.

24 Claims, 5 Drawing Sheets

U.S. PATENT DOCUMENTS

| | | | |
|---|---|---|---|
| 5,820,589 A | 10/1998 | Torgerson et al. | |
| 5,893,838 A | 4/1999 | Daoud et al. | |
| 5,899,873 A | 5/1999 | Jones et al. | |
| 5,928,195 A | 7/1999 | Malamud et al. | |
| 5,999,857 A | 12/1999 | Weijand et al. | |
| 6,179,806 B1 | 1/2001 | Sansoucy | |
| 6,203,523 B1 | 3/2001 | Haller et al. | |
| 6,551,290 B1 | 4/2003 | Elsberry et al. | |
| 6,585,681 B2 | 7/2003 | Brugger et al. | |
| 6,689,085 B1 * | 2/2004 | Rubenstein et al. | 604/9 |
| 6,749,581 B2 | 6/2004 | Thompson et al. | |
| 6,893,429 B2 | 5/2005 | Petersen | |
| 6,945,969 B1 | 9/2005 | Morris et al. | |
| 2002/0107471 A1 | 8/2002 | Thompson et al. | |
| 2004/0199128 A1 | 10/2004 | Morris et al. | |
| 2005/0075624 A1 | 4/2005 | Miesel | |
| 2005/0090799 A1 | 4/2005 | Morris | |
| 2005/0241387 A1 | 11/2005 | Miesel et al. | |
| 2005/0245867 A1 | 11/2005 | Olsen et al. | |
| 2005/0245887 A1 | 11/2005 | Olsen et al. | |

FOREIGN PATENT DOCUMENTS

| | | |
|---|---|---|
| EP | 0 873 762 A | 10/1998 |
| EP | 0 968 732 A | 1/2000 |

\* cited by examiner

BRANCHING CATHETER SYSTEMS WITH DIAGNOSTIC COMPONENTS

RELATED APPLICATION

This application claims the benefit of U.S. Provisional Application No. 60/564,473, titled CATHETER SYSTEM HAVING FLOW RESTRICTION, AND DIAGNOSTIC SYSTEM FOR USE WITH SAME, filed Apr. 22, 2004, which is hereby incorporated by reference in its entirety.

TECHNICAL FIELD

The present invention relates generally to implantable medical devices and, more particularly, to branching catheter systems that include diagnostic components for detecting and isolating fluid flow problems (e.g., leaks, occlusions, etc.).

BACKGROUND

Implantable drug infusion systems are used to provide programmable long-term delivery of a therapeutic agent, e.g., infusate drug, to a target site such as the brain or the spinal canal or epidural space. These systems typically include a pump implanted at a remote location, e.g., within the abdominal or chest cavity, and a catheter tunneled from the pump to the target site. A drug may be delivered from a reservoir in the pump to the target site via the catheter.

Some therapies, e.g., treatment of many neurological diseases, may benefit from infusion of a therapeutic agent to multiple locations within the body. For instance, for the treatment of Parkinson's Disease, it may be beneficial to deliver a substance, e.g., Glial Derived Neurotrophic Factor (GDNF), to both hemispheres of the brain (bilaterally). Infusing a drug to such multiple target sites is typically accomplished by separate infusion systems, e.g., a separate pump and catheter system for each target site. However, duplicate systems result in not only increased costs and patient invasiveness (as compared to single target site systems), but also increased complexity that is inherent in such dual systems.

Branching catheter systems such as those described in, e.g., U.S. Patent Application Publication No. US 2004/0199128 A1 (Morris et al.) and titled CATHETER FOR TARGET SPECIFIC DRUG DELIVERY, have been developed to address some of the issues associated with using multiple systems for delivering drugs to multiple locations within a patient.

SUMMARY OF THE INVENTION

The present invention is directed at branching catheter systems with diagnostic components for detecting and isolating fluid flow problems (e.g., leaks, occlusions, etc.) and methods for detecting and isolating fluid flow problems. Among the fluid flow problems that may potentially be detected are leaks in the branching catheter systems (e.g., cuts, disconnected components, etc.). Another fluid flow problem that may be detected using the diagnostic systems of the present invention is the presence of occlusions or other blockages that prevent fluid flow within the catheter systems. In addition to identifying that a problem exists, the diagnostic components may preferably also be used to identify the location of the fluid flow problem as discussed herein.

Among the diagnostic components that may be used in branching catheter systems of the present are valves to control fluid flow through the various sections of the branching catheter system, fluid flow detectors to detect flow through the one or more sections of the branching catheter system and a control system for operating the diagnostic components.

In some embodiments, the diagnostic components may preferably include a supply valve to control flow to all of the branches of the branching catheter and branch valves in each of the branches to control the flow of fluid into the selected branch. The valves may preferably operate as shut-off valves to occlude flow at the their location within the branching catheter system.

The flow detector may preferably be positioned and operable to detect fluid flow delivered by a pump mechanism. The flow detector may take a variety of different forms, e.g., a pressure sensor operable to sense pressure at a location within the catheter system (where pressure is indicative of flow), a flow sensor operable to detect fluid moving through a lumen (e.g. a mass flow sensor), etc.

Branching catheter systems that incorporate diagnostic components of the present invention may preferably include a branching catheter connector that includes an inlet port and two or more outlet ports in fluid communication with the inlet port. Each of the outlet ports may preferably feed fluid into a branch of the branching catheter system, while the inlet port may preferably be adapted to receive fluid from a pump mechanism operably connected to a reservoir containing a supply of a drug to be delivered to a patient.

Although it may be preferred that the branching catheter systems include diagnostic components such as valves to control fluid flow past a selected point, methods of the present invention may alternatively involve manual occlusion of lumens at selected locations within the branching catheter systems. For example, occlusion may involve manual compression of a catheter at a selected location such that the catheter is pinched at that location.

In another embodiment, a method for detecting and isolating leaks and occlusions in a branching catheter system is provided. The method may include detecting a change in a characteristic, e.g., pressure, of a fluid within the system. Valves associated with one or more of an inlet port, a first outlet port, and a second outlet port of a branching connector of the system may be activated independently to disrupt flow through one or more sections of the system. The method may also include monitoring fluid flow (e.g., pressure) after valve activation; and determining a location of a catheter leak and/or occlusion based upon the pressure detected.

To assist in diagnosis of fluid flow problems in branching catheters, it may be preferred to include flow restrictors at selected locations within the branching catheters. In addition to assisting with diagnosis of fluid flow problems, the flow restrictors may also be useful for balancing flow between different branches in a branching catheter system.

Branching catheter systems including diagnostic components in accordance with the present invention or methods of the present invention may provide intuitive and systematic techniques, in conjunction with appropriate hardware, for troubleshooting infusion systems including implantable branching catheter systems. For example, the systems and/or methods as described herein may be used to detect catheter failures as well as identify failure locations in branching catheter systems. In other words, these systems and/or methods may enable not only detection of a catheter failure, e.g., the presence of a leak or clog, but may also isolate that failure to a particular section (i.e., supply catheter or specific branch catheter) of the branching catheter system.

The systems and/or methods of the present invention may also allow confirmation of successful implantation while the patient is still on the operating table. Moreover, revision surgeries to correct problems can be focused to the appropriate component(s) of the system, thus making surgery potentially less invasive and time consuming.

In addition to potentially increased robustness of the implant procedure and potentially improved ability to focus repairs/revisions, the systems and/or methods as described herein may also reduce the risk of patient over/under dosing. Moreover, these systems and/or methods may decrease the number of instances of therapies that might be inappropriately discontinued as "inefficacious" or classified as "marginally efficacious." By using the feedback provided by systems and/or methods of the present invention, physicians may further be able to develop improvements in implant technique and hardware design.

In one embodiment, a flow restrictor for use with an implantable catheter of the present invention may include an elongate male member having a helical groove formed in an outer surface thereof. The flow restrictor may fit with interference within a lumen of a catheter or other device or, alternatively, may fit with interference inside a separate sheath, wherein the combined restrictor/sheath may then be inserted within the catheter lumen.

The fluids delivered using the present invention may preferably contain one or more drugs. A drug of the present invention may include a therapeutic substance. Other substances may or may not be intended to have a therapeutic effect and are not easily classified, such as, e.g., saline solution, fluoroscopy agents, disease diagnostic agents, etc. Unless otherwise noted in the following paragraphs, the term "drug" as used herein may include any therapeutic, diagnostic, or other substance that is delivered using the implantable medical devices of the present invention. The drugs will typically be fluids (e.g., liquids) or contained in fluid carriers (e.g., liquid carriers) as either solutions or mixtures.

Therapeutic substances delivered using the present invention may preferably be intended to have a therapeutic effect such as pharmaceutical compositions, genetic materials, biologics, and other substances. Pharmaceutical compositions are typically chemical formulations intended to have a therapeutic effect such as intrathecal antispasmodics, pain medications, chemotherapeutic agents, and the like. Pharmaceutical compositions may be configured to function in an implanted environment with characteristics such as stability at body temperature to retain therapeutic qualities, concentration to reduce the frequency of replenishment, and the like. Genetic materials include substances intended to have a direct or indirect genetic therapeutic effect such as genetic vectors, genetic regulator elements, genetic structural elements, DNA, and the like. Biologics include substances that are living matter or derived from living matter intended to have a therapeutic effect such as stem cells, platelets, hormones, biologically produced chemicals, and the like.

In one aspect, the present invention provides an implantable branched catheter system that includes a supply catheter section having a proximal end and a distal end and two or more delivery branches in fluid communication with the distal end of the supply catheter section. Each delivery branch of the two or more delivery branches includes a delivery catheter section having a proximal end and a distal end along with a flow restrictor located along the delivery catheter section, wherein the flow restrictor restricts flow through the delivery catheter section. Each delivery branch further includes a branch valve located between the distal end of the supply catheter section and the proximal end of the delivery catheter section. The system also includes a supply valve located proximate the distal end of the supply catheter section, wherein the supply valve controls flow through the distal end of the supply catheter section; and a flow detector located proximate the proximal end of the supply catheter section, wherein the flow detector detects flow through the supply catheter section.

In another aspect, the present invention provides an implantable branched catheter system that includes a supply catheter section having a proximal end and a distal end and two or more delivery branches in fluid communication with the distal end of the supply catheter section. Each delivery branch of the two or more delivery branches includes a delivery catheter section having a proximal end and a distal end; a flow restrictor located proximate a distal end of the delivery catheter section, wherein the flow restrictor restricts flow through the delivery catheter section; and a branch valve located between the distal end of the supply catheter section and the proximal end of the delivery catheter section. The system further includes a supply valve located proximate the distal end of the supply catheter section, wherein the supply valve controls flow through the distal end of the supply catheter section and a bleeder valve located proximate the distal end of the supply catheter section, wherein the bleeder valve is located distal of the supply valve, and wherein the bleeder valve shunts flow out of the branched catheter system. The system also includes a flow detector located proximate the proximal end of the supply catheter section, wherein the flow detector is a pressure sensor.

In another aspect, the present invention provides a branching catheter connector for use in an implantable branching catheter system, the connector including an implantable connector body defining a fluid path having a branch point at which the fluid path separates into two or more branches; an inlet port located within the connector body, the inlet port in fluid communication with the fluid path; two or more outlet ports in fluid communication with the inlet port through the branching fluid path, wherein the branch point is located between the inlet port and the two or more outlet ports; a supply valve located proximate the inlet port, wherein the supply valve is located in the branching fluid path between the inlet port and the branch point; and a branch valve located proximate each outlet port of the two or more outlet ports, wherein the branch valve of each outlet port is located in the fluid path between the branch point and the outlet port.

In another aspect, the present invention provides a method of diagnosing flow conditions in a branched catheter system. The method includes providing an implantable branched catheter system that includes a supply catheter section having a proximal end and a distal end, wherein moving from the proximal end towards the distal end defines a downstream direction within the system and wherein moving from the distal end towards the proximal end defines an upstream direction within the system. The system further includes a flow detector located proximate the proximal end of the supply catheter section, wherein the flow detector detects flow through the supply catheter section; and two or more delivery branches in fluid communication with the distal end of the supply catheter. Each delivery branch of the two or more delivery branches includes a delivery catheter section having a proximal end and a distal end, and wherein each delivery branch of the two or more delivery branches includes a flow restrictor located within the delivery branch, wherein the flow restrictor restricts flow through the delivery catheter section. The method further includes delivering fluid into the proximal end of the supply catheter section; and monitoring the flow detector while delivering the fluid and while selectively occluding flow through one or more of the supply catheter section and the delivery catheter sections.

In another aspect, the present invention provides a method of diagnosing flow conditions in a branched catheter system.

The method includes providing an implantable branched catheter system that includes a supply catheter section having a proximal end and a distal end, wherein moving from the proximal end towards the distal end defines a downstream direction within the system and wherein moving from the distal end towards the proximal end defines an upstream direction within the system. The system further includes a flow detector located proximate the proximal end of the supply catheter section, wherein the flow detector detects flow through the supply catheter section; and two or more delivery branches in fluid communication with the distal end of the supply catheter. Each delivery branch of the two or more delivery branches includes a delivery catheter section having a proximal end and a distal end, and wherein each delivery branch of the two or more delivery branches includes a flow restrictor located proximate a distal end of the delivery branch, wherein the flow restrictor restricts flow through the delivery catheter section. The method further includes delivering fluid into the proximal end of the supply catheter section; and monitoring the flow detector while delivering the fluid and while selectively occluding flow through one or more of the supply catheter section and the delivery catheter sections. The method further comprises selectively shunting the fluid delivered into the supply catheter section outside of the system before the fluid enters the two or more delivery branches while monitoring the flow detector The above summary is not intended to describe each embodiment or every implementation of the present invention. Rather, a more complete understanding of the invention will become apparent and appreciated by reference to the following Detailed Description of Exemplary Embodiments in view of the accompanying figures of the drawing.

BRIEF DESCRIPTIONS OF THE FIGURES.

The present invention will be further described with reference to the figures, wherein.

DETAILED DESCRIPTION OF EXEMPLARY EMBODIMENTS

Figure 1:
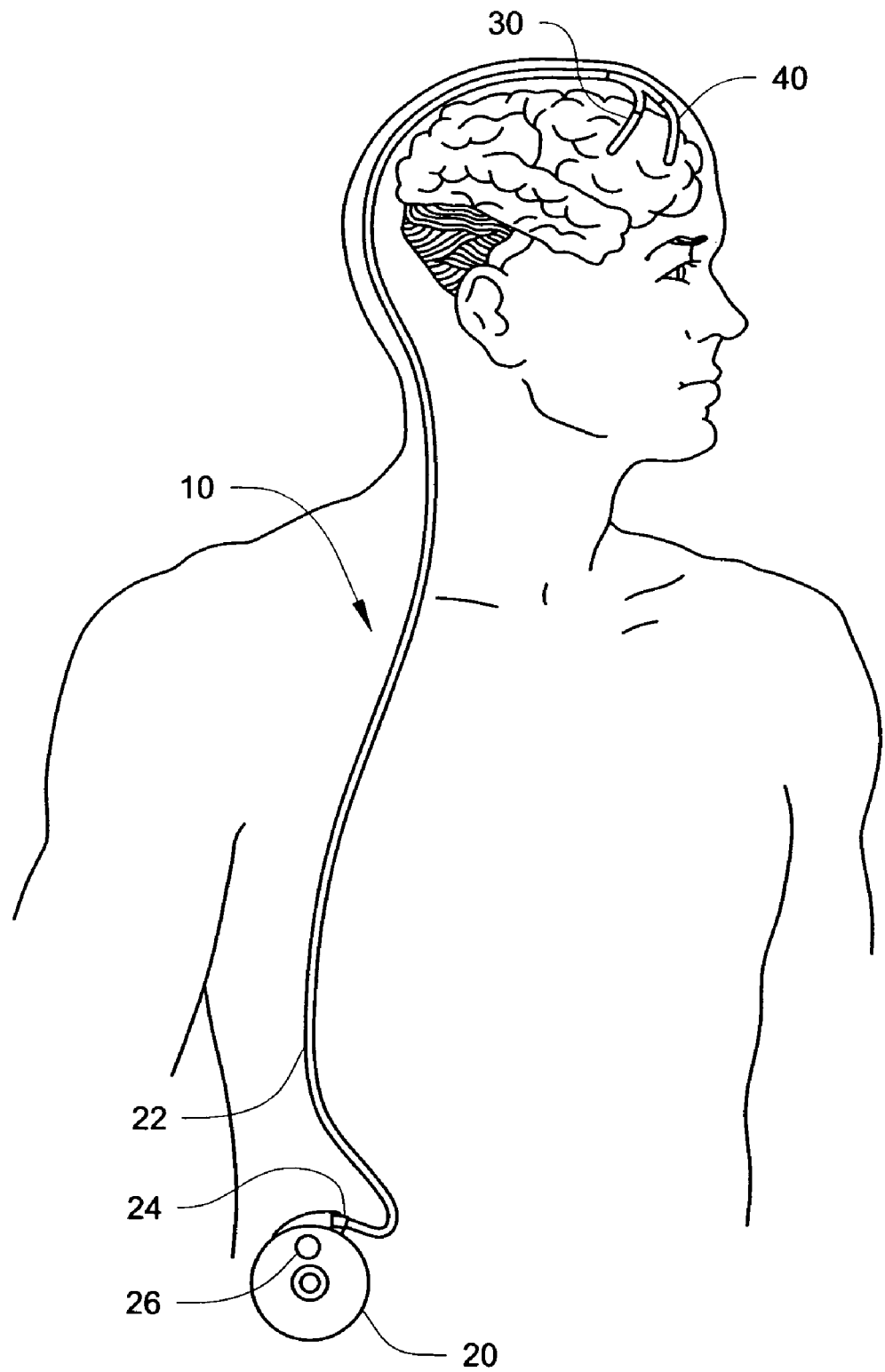
FIG. 1 is a diagrammatic representation of an implanted branching catheter system in accordance with one embodiment of the invention.

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

Catheter cuts, occlusions, kinks, and improper (e.g. leaking) connections together may represent a substantial portion of clinical complications with current implantable infusion systems. Such problems may be aggravated for infusion systems delivering drugs to one or more locations (e.g., branching catheter systems) that utilize a fixed rate pump because, for example, complete occlusion of one distal branch could result in the delivery of the full balance of the drug to the other branch. Normal techniques of detecting an occlusion in a single catheter system, such as syringe extraction of the reservoir volume and subsequent comparison of the same to the expected volume, would be inaccurate in these circumstances as the appropriate volume would still be dispensed, albeit to only a single side. Embodiments of the present invention as described herein preferably enable reliable diagnosis of the above-mentioned problems, whether they were induced immediately as a inadvertent consequence of implantation, or occurred during the course of therapy.

FIG. 1 illustrates an exemplary implanted branching catheter system 10 in accordance with one embodiment of the invention. The system 10 may include a device, e.g., a pump 20, implanted in an abdominal region of a patient, and a proximal infusion catheter 22, coupled to the pump 20 via a connector 24. The proximal catheter 22 may extend into the head of the patient, where fluid flow may be divided into two branches 30 and 40, with each branch including a branch catheter implanted to deliver the fluid to separate areas of the brain.

Although the embodiment of FIG. 1 includes a bifurcating catheter system, the present invention may include catheter systems with three or more branches. In other variations, although the depicted system is implanted for delivery into the brain of a patient, it should be understood that branching catheter systems of the present invention may be used to deliver fluids to other areas of the body.

Furthermore, although the pump 20 is depicted as implanted within the abdominal cavity, it may alternatively be implanted in any suitable location, e.g., in the chest cavity, cranially, etc. In some instances, the pump mechanism itself may not even be implanted, i.e., the pump 20 may be located externally of the patient's body, with the catheter 22 used to deliver the fluid internally.

The pump 20 may include a reservoir to hold a volume of fluid that may preferably contain one or more drugs. The reservoir may be periodically refilled via an injection port (not shown), and a pump mechanism (e.g., pressurized bladder, peristaltic pump, piston pump, etc.) provided may propel the fluid through the proximal catheter 22 and into the branches 30 and 40. While not wishing to be bound to any particular configuration, the pump 20 may be a SYNCHROMED II manufactured by Medtronic, Inc., of Fridley, Minn., USA.

The pump 20 may further include a flow detector 26, e.g., a pressure sensor. The pressure sensor may be similar to that described in U.S. Patent Application Publication No. US 2005/0075624 A1, entitled "Pressure Sensor for Medical Device" (see also: U.S. patent application Ser. No. 10/691,814, filed 23 Oct. 2003, and entitled "Method for Monitoring Bolus Delivery;" U.S. Pat. No. 6,551,290, entitled "Catheter for Target Specific Drug Delivery;" and U.S. patent application Ser. No. 09/625,751, filed 26 Jul. 2000, and entitled "Catheter for Target Specific Drug Delivery"). Alternatively, the flow sensing device could detect fluid flow directly using any appropriate flow detection technologies.

Figure 2:
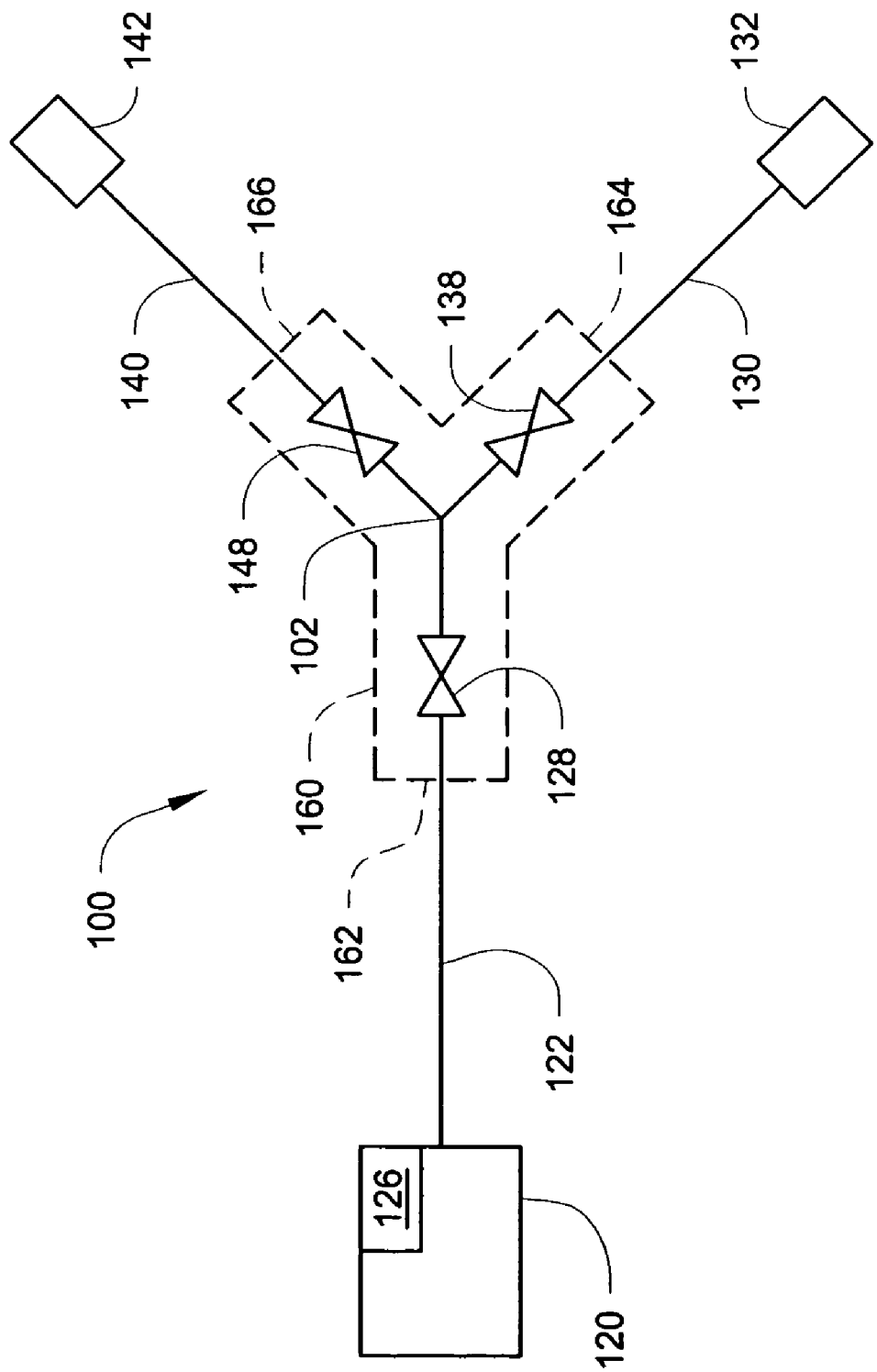
FIG. 2 is a schematic diagram of one exemplary branching catheter system according to the present invention.
Figure 3:
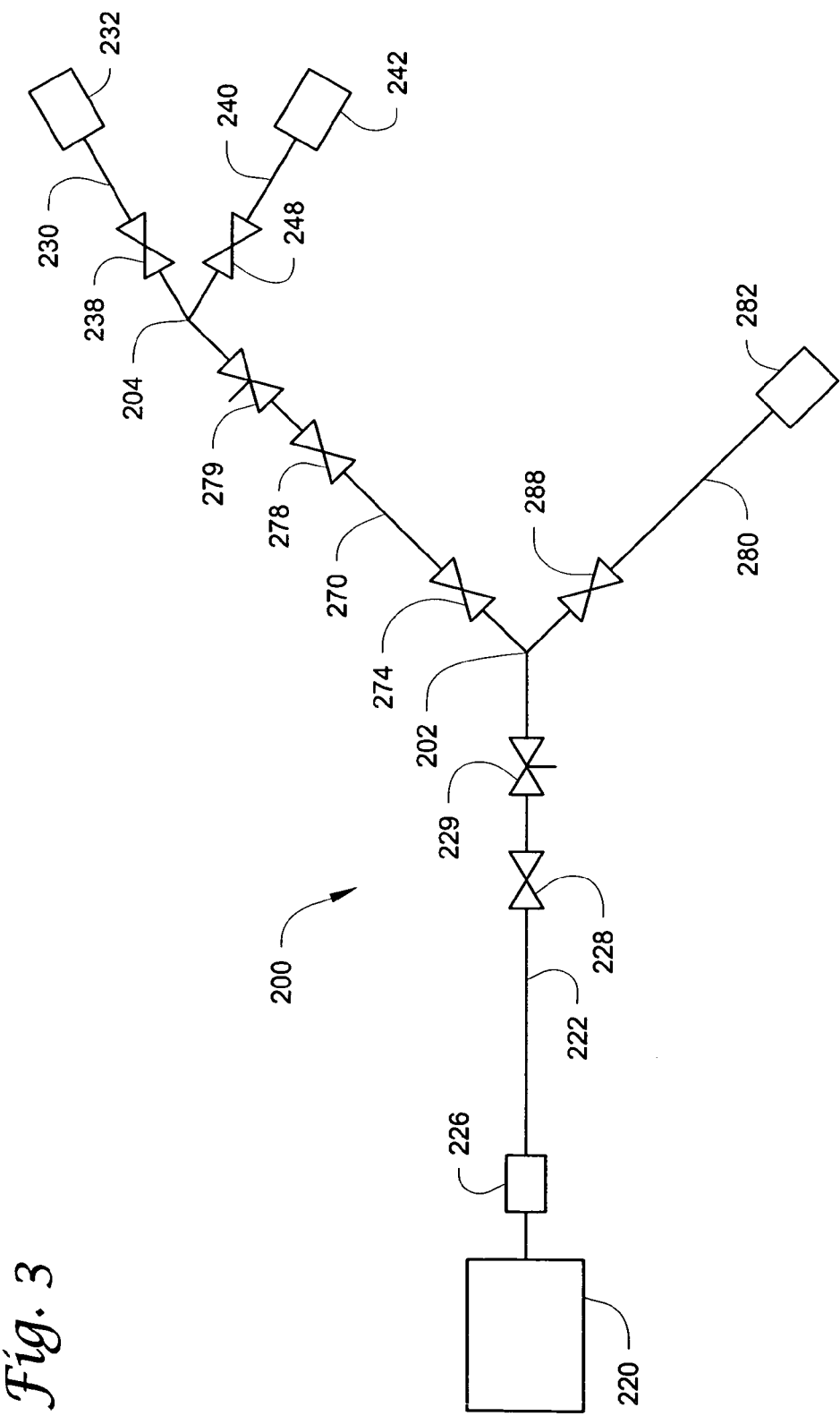
FIG. 3 is a schematic diagram of another exemplary branching catheter system according to the present invention.

FIGS. 2 & 3 are schematic diagrams of two examples of branching catheter systems according to the present invention. The various components of the two branching catheter systems will be described below, followed by a description of a third example depicted in FIG. 4. Operation of a branching catheter system and its diagnostic components will be described with respect to the system depicted in FIG. 4.

The branching catheter system 100 of FIG. 2 includes a supply catheter 122 that leads to two branches with branch catheters 130 and 140. The supply catheter 122 of the branching catheter system 100 is depicted as attached to a pump 120, although it should be understood that the branching catheter systems of the present invention may be supplied independently of the pump mechanisms used to deliver fluids into the branching catheter systems.

Although described herein as catheters, it should be understood that the supply catheters and delivery catheters or branch catheters of some embodiments may be sections of a branching catheter system as opposed to separate independent components assembled into the branching catheter systems. In other words, the different catheters may be sections of an integrally formed catheter system. Alternatively, one or more of the different catheters may be provided as separate components that are assembled to provide a branching catheter system according to the present invention.

As discussed herein, the pump 120 may take any suitable configuration and may preferably include a reservoir containing a drug for delivery to a patient. Also depicted in FIG. 2 is a flow detector 126 used to detect flow into the branching catheter system 100. The flow detector 126 is depicted as integral with the pump mechanism 120, although it may be provided separately from the pump 120. It may, however, be preferred that the flow detector 126 (if separate from the pump 120) be located close to the pump 120, because, as discussed herein, diagnostics can typically be performed only on components of the branching catheter system that are located downstream of the flow detector 126.

The system 100 of FIG. 2 also includes valves used to control fluid flow within the system. It may be preferred that the valves prevent flow when closed, although in some instances, it may be sufficient if some small amount of fluid passes through the valves when closed. The depicted system 100 includes a supply valve 128 that is preferably located proximate the distal end of the supply catheter 122. Branch valves 138 and 148 are located within each of the branches 130 and 140, respectively. It may be preferred that the branch valves 138 and 148 be located as close as possible to the branch point 102 at which fluid is divided to flow into the branch catheters 130 and 140.

Each of the branches 130 and 140 may also preferably include a flow restriction 132 and 142, respectively. The flow restrictors may preferably serve to: a) ensure balanced delivery of infusate (fluid) through the branches of the system; and/or b) provide sufficient backpressure to ensure robust detection of fluid flow problems such as cuts/occlusions. Further discussions regarding the use of flow restrictors in branched catheters may be found in U.S. Patent Application Publication No. US 2004/0199128 A1 (Morris et al.), entitled CATHETER FOR TARGET SPECIFIC DRUG DELIVERY. As described therein, the flow restrictors may be in the form of a component that functions to both provide flow restriction and deliver a drug to a selected body location (using, e.g., a permeable membrane, small orifices, etc.). Alternatively, fluid delivery out of the catheter and flow restriction of fluid moving through the catheter may be performed by separate components.

The term "flow restrictor" as used herein, is intended to represent a flow resistance that is added to a system to bring the total flow resistance above a specified value; it does not necessarily refer to a singular component. For example, two "flow restrictors" (i.e. two components) of equal resistance placed in series at the tip of a given catheter could be functionally equivalent to a single flow restrictor whose resistance is twice that of either of the serial flow restrictors taken by itself.

The various components such as valves, pumps, etc. in systems according to the present invention may be controlled by any suitable controller that may be implanted in or located outside of the body of the patient. For example, the controller may be located within the pump 120 or external thereto and connected to the various components by wires, optical fibers, etc. Control may also be effected by the use of telemetry, which may be used for communication between components and a user, for external programming etc. Telemetry control devices, systems and methods that may be adapted for use in connection with the present invention may be described in, e.g., U.S. Pat. Nos. 5,558,640 (Pfeiler et al.); 5,820,589 (Torgerson et al.); and 5,999,857 (Weijand et al.).

Also depicted in broken lines in FIG. 2 is a branching catheter connector 160 that may be used in connection with branching catheter systems of the present invention. The connector 160 may house the supply valve 128 and branch valves 138 and 148, as well as the branch point 102 at which fluid flowing through the system 100 is divided for delivery to the different branches 130 and 140.

The body of the connector 160 may, in one embodiment, be made from molded silicone (e.g., Nu-Sil MED 4870 LSR, 65-75 Shore A durometer). This material may provide certain potentially desirable benefits, e.g., desirable material properties such as elastic and creep characteristics, at a relatively low cost. However, other biocompatible materials such as ETR silicone, urethane, polyurethane, etc., are also possible without departing from the scope of the invention.

Use of the connector 160 may be advantageous in that the connector 160 may be provided as an independent component that can be assembled with existing catheters to form a branching catheter system according to the present invention. As a result, an existing catheter or tubing may be used as the supply catheter 122 connecting the pump 120 to the inlet port 162 of the connector 160. Similarly, existing catheters may also be connected to the outlet ports 164 and 166 of the connector to provide branch catheters 130 and 140. The connector 160 may preferably define a fluid path that includes the branch point 102, inlet port 162 and outlet ports 164 and 166. The various valves may preferably be distributed along the fluid path as defined within the connector 160. For example, a bleeder valve (see ZA2 in FIG. 4) may be located in the fluid path between the supply valve 128 and the branch point 102. Similarly a controller may be operatively connected to the valves and other components in the connectors of the present invention.

FIG. 3 is a schematic diagram of another branching catheter system 200 that includes more than two branches. The branching catheter system 200 is attached to a pump mechanism 220 using a supply catheter 222. A flow detector 226 is located proximate the proximal end of the supply catheter 222. In this embodiment, the flow detector 226 is depicted as separate from the pump mechanism 220.

The supply catheter leads to the first branch point 202 at which the fluid flow separates into two branch catheters 270 and 280. A supply valve 228 is, however, preferably located upstream of the branch point 202. As with branching catheter system 100, it may also be preferred that the valve 228 be located proximate the distal end or downstream end of the supply catheter 222.

An optional component depicted in the branching catheter system 200 is a bleeder valve 229. The bleeder valve 229 preferably functions to prevent flow to the branch point 202 and also to shunt or divert flow out of the branching catheter system 200. Use of the bleeder valve 229 may allow for the detection of an occlusion in the supply catheter 222 located between the flow detector 226 and the bleeder valve 229 as described elsewhere herein. Although the valve 228 and bleeder valve 229 are depicted as separate components, it will be understood that they may be integrated into a single valve mechanism (e.g., a three port valve) that can perform the functions of both valves 228 and 229.

The branching catheter system 200 also includes branch valves 274 and 288 downstream of the branch point 202. It may be preferred that the branch valves 274 and 288 be capable of shutting off or occluding flow into their respective branch catheter 270 or 280. As a result, it may be preferred that the branch valves 274 and 288 be located as close as possible to the upstream or proximal ends of the branch catheters 270 and 280 such that the branch catheters can be isolated from the branching catheter system 200.

Branch catheter 280 in the depicted branching catheter system 200 also preferably includes a flow restrictor 282. It may be preferred that the flow restrictor 282 be located proximate the distal end of the branch catheter 280 as depicted in FIG. 3.

Branch catheter 270 in the depicted branching catheter system 200 leads to a second branch point 204 from which branch catheters 230 and 240 extend. As a result, the branch catheter 270 may function in many respects like supply catheter 222. For example, the branch catheter 270 may also preferably include a valve 278 proximate its distal or downstream end, i.e., the end at which fluid flow is divided by the branch point 204. The branch catheter 270 may also preferably include a bleeder valve 279 proximate its distal end similar to the supply catheter 222. As with supply catheter 222, the valve 278 and bleeder valve 279 are depicted as separate components, although it will be understood that they may be integrated into a single valve mechanism (e.g., a three port valve) that can perform the functions of both valves 278 and 279.

Branch valves 238 and 248 are preferably provided within each of the branch catheters 230 and 240, respectively, downstream from the branch point 204. It may be preferred that the branch valves 238 and 248 be located as close as possible to the branch point 204 at which fluid is divided to flow into the branch catheters 230 and 240. Each of the branch catheters 230 and 240 may also preferably include a flow restrictor 232 and 242, respectively. It may be further preferred that the flow restrictors be located at or near the distal ends of the branch catheters 230 and 240.

The branching catheter system 200 include three delivery branches in branch catheters 230, 240 and 280. As discussed above, it may be preferred that each of the branch catheters include a flow restrictor 232, 242, and 282 (respectively). If it is desired that the amount of fluid (i.e., drug) to be delivered from each of the three branches is to be roughly equal, the flow restrictors may not necessarily be identical. It may be necessary, for example, to consider the effects of the valves and the length of the fluid flow path through the different catheters and adjust the amount of flow restriction provided in each of the branches to balance flow therethrough.

Figure 4:
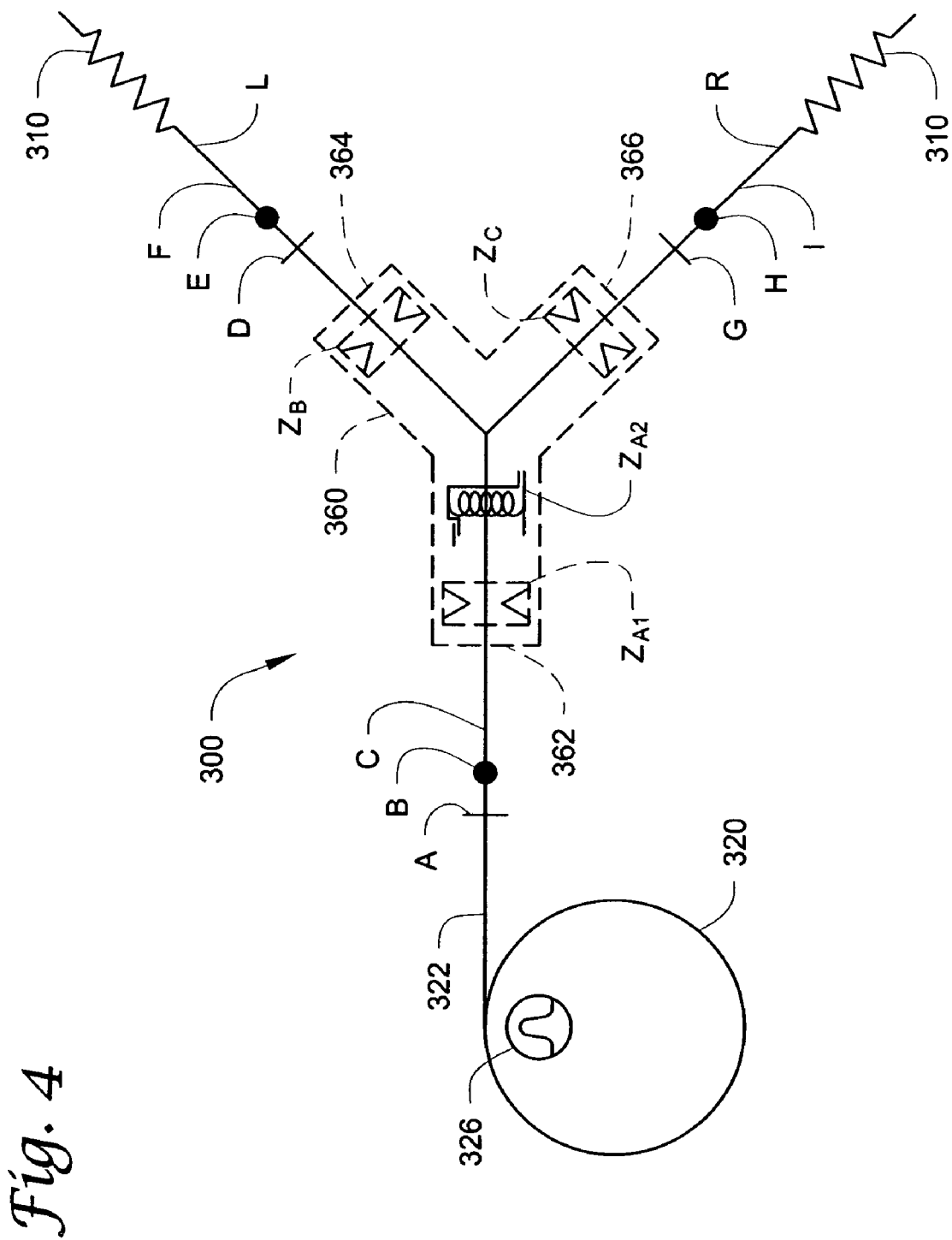
FIG. 4 is a schematic diagram of another exemplary branching catheter system according to the present invention.

FIG. 4 s a schematic diagram of another branching catheter system 300 including diagnostic components that is attached to a pump 320. Fluid is delivered to the branching catheter system 300 using a proximal or supply catheter 322 that may preferably be connected to an inlet port 362 of a branching catheter connector 360. The pump 320 may preferably include a flow detector 326, e.g., a pressure sensor operable to monitor pump output pressure. The proximal catheter 322 may be fluidly coupled, via the connector 360, to a left outlet port 364 that is, in turn, coupled to a first or left branch catheter L. The proximal catheter 322 may also be coupled, via the connector 360, to a right outlet port 366 that is, in turn, coupled to a second or right branch catheter R.

A flow restrictor 310 may preferably be located near a distal end of each branch catheter L and R. As described above, the flow restrictors may preferably serve to: a) ensure balanced delivery of infusate to the target regions; and/or b) provide sufficient backpressure to ensure robust detection of cuts/occlusions by the pressure sensor.

Along with the flow detector 326 and the flow restrictors 310, the diagnostic system may include a series of valves to assist in the diagnosis of fluid flow problems within the branching catheter system 300. In the embodiment of branching catheter system 300 depicted in FIG. 4, valves ZA1 (located proximate the inlet port 362 of the connector 360), ZB (located in the left outlet port 364 of connector 360), and ZC (located in the right outlet port 366 of connector 360) may preferably, when activated, impede flow (and more preferably prevent flow past the valve). For example, the valves may preferably be pinch-type, shut-off valves, although any suitable valve construction may be used.

Also, although the valves may preferably be used while performing methods of the present invention, it should be understood that the methods may alternatively be performed using manual pressure on a selected segment of catheter tubing down (against a hard surface, e.g., the cranium) in order to block flow.

Optional valve ZA2 as seen proximate the inlet port 362 of the connector 360 may preferably be a bleeder valve. That is, when activated, valve ZA2 may preferably both shut off flow downstream of the valve and shunt the flow path outside the catheter system 300, e.g., into surrounding tissue. In some embodiments, the shut-off feature of valve ZA2 may be eliminated, i.e., it may function as a bleeder valve only. In other embodiments, valve ZA2 could be eliminated altogether. If no bleeder valve is present, methods as described below in which the bleeder valve ZA2 is activated could alternatively be practiced by, e.g., unplugging (disconnecting) the supply catheter 322 from the connector 360). However, by providing the bleeder valve ZA2, a physician may preferably have the ability to perform a wide range of diagnostics without having to perform, e.g., subcutaneous cut-down to access the proximal catheter 322 to disconnect it manually.

In some embodiments in which, e.g., the branching catheter system 300 is implanted cranially, the valves ZA1, ZA2, ZB, and ZC may preferably be felt beneath the skin of the scalp after implantation. In such a situation, the valves may be actuated by manually compressing the valve against a surface such as the cranium or other surface that allows for sufficient compression to close the valve.

Valves ZA1-ZC could be configured as separate metal or plastic components located inside the respective ports of the connector 360. Alternatively, the valves could be integrally formed with the connector 360, e.g., as part of the molded structure itself. Shunting hardware for managing hydrocephalic patients provide examples of the latter.

In FIG. 4, reference letters A, B, C, D, E, F, G, H, and I are used to identify catheter fluid flow status. In particular, reference letters A, D, and G are used to identify a cut in the supply catheter 322, the left catheter L, and the right catheter R, respectively. Similarly, reference letters B, E, and H are used to identify an occlusion in the supply catheter 322, the left catheter L, and the right catheter R, respectively. Finally, reference letters C, F, and I are used to identify the supply catheter 322, the left catheter L, and the right catheter R, respectively, as being normal or intact.

Figure 5:
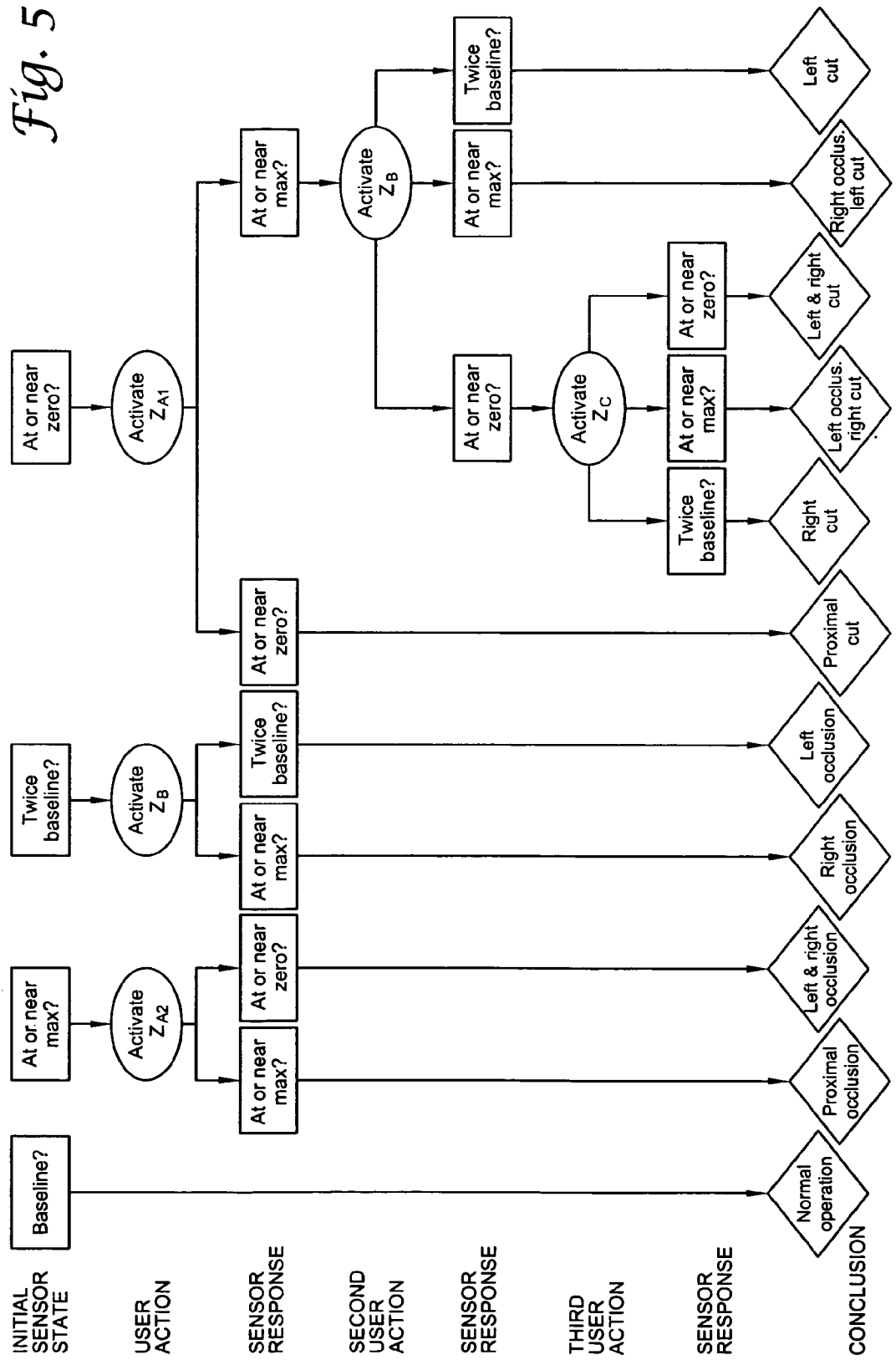
FIG. 5 is a flow chart illustrating an exemplary method of identifying and locating a fluid flow problem within the branching catheter system of FIG. 4.

The configuration of the branching catheter system 300 depicted in FIG. 4 permits twenty-seven (27) possible status combinations, i.e., combinations of cuts, occlusions, and intact (free of cuts or occlusions) catheter portions. These combinations are presented in tabular form in Table I. Each status combination can be distinguished from the others by some set of user actions. For example, FIG. 5 illustrates a flow chart describing the sensor states and user actions of Table I, as well as the resulting conclusions that may be drawn therefrom. However, these cases are not a unique set. For example, redundant (i.e. unnecessary or inconclusive actions) might be performed before entering one of the paths shown in the flow chart of FIG. 5.

However, where the initial sensor state is at or near maximum (i.e., at or near the maximum pressure output of the pump 320) as shown in the second column of the flowchart of FIG. 5; is about twice the baseline pressure as shown in the third column of FIG. 5; or is at or near zero pressure as shown in the fourth column of FIG. 5, additional valve activation/manipulation may reveal the existence of a fluid flow problem within the branching catheter system 300 (e.g., catheter cut or occlusion). If the flow detector and valves are in the preferred locations as discussed herein, it may also be possible to identify the general location of the fluid flow problem (e.g., in the supply catheter 322 and/or branch catheters L & R).

TABLE I

| Case | Supply Leg (322) | Left Leg (L) | Right Leg (R) | Initial Sensor State (326) | User Action(s) (Activated Valve(s)) → Corresponding Sensor Response(s) |
|------|------|------|------|------|------|
| 1 | A | D | G | TO ZERO | $Z_{A1}$ → TO ZERO |
| 2 | A | D | H | TO ZERO | $Z_{A1}$ → TO ZERO |
| 3 | A | D | I | TO ZERO | $Z_{A1}$ → TO ZERO |
| 4 | A | E | G | TO ZERO | $Z_{A1}$ → TO ZERO |
| 5 | A | E | H | TO ZERO | $Z_{A1}$ → TO ZERO |
| 6 | A | E | I | TO ZERO | $Z_{A1}$ → TO ZERO |
| 7 | A | F | G | TO ZERO | $Z_{A1}$ → TO ZERO |
| 8 | A | F | H | TO ZERO | $Z_{A1}$ → TO ZERO |
| 9 | A | F | I | TO ZERO | $Z_{A1}$ → TO ZERO |
| 10 | B | D | G | TO MAX | $Z_{A2}$ → TO MAX |
| 11 | B | D | H | TO MAX | $Z_{A2}$ → TO MAX |
| 12 | B | D | I | TO MAX | $Z_{A2}$ → TO MAX |
| 13 | B | E | G | TO MAX | $Z_{A2}$ → TO MAX |
| 14 | B | E | H | TO MAX | $Z_{A2}$ → TO MAX |
| 15 | B | E | I | TO MAX | $Z_{A2}$ → TO MAX |
| 16 | B | F | G | TO MAX | $Z_{A2}$ → TO MAX |
| 17 | B | F | H | TO MAX | $Z_{A2}$ → TO MAX |
| 18 | B | F | I | TO MAX | $Z_{A2}$ → TO MAX |
| 19 | C | D | G | TO ZERO | $Z_{A1}$ → TO MAX; $Z_B$ → TO ZERO; $Z_C$ → TO ZERO |
| 20 | C | D | H | TO ZERO | $Z_{A1}$ → TO MAX; $Z_B$ → MAX |
| 21 | C | D | I | TO ZERO | $Z_{A1}$ → TO MAX; $Z_B$ → TWICE BASELINE |
| 22 | C | E | G | TO ZERO | $Z_{A1}$ → TO MAX; $Z_C$ → MAX |
| 23 | C | E | H | TO MAX | $Z_{A2}$ → TO ZERO |
| 24 | C | E | I | TWICE BASELINE | $Z_C$ → TO MAX |
| 25 | C | F | G | TO ZERO | $Z_{A1}$ → TO MAX; $Z_C$ → TWICE BASELINE |
| 26 | C | F | H | TWICE BASELINE | $Z_B$ → TO MAX |
| 27 | C | F | I | BASELINE | BASELINE |

The following examples may illustrate an exemplary procedure for utilizing the diagnostic system illustrated in FIG. 4. Once implanted, the flow detector 326 of the branching catheter system 300 may be interrogated, e.g., via telemetry or other techniques, to ascertain what is referred to herein as an "initial sensor state." It may, for example, be desirable to interrogate the flow detector 326 during or immediately after implantation to ensure that the branching catheter system 300 is intact and functional. Similarly, it may be beneficial over the course of treatment to interrogate the flow detector 326 of the branching catheter system 300 if patient response indicates a potential problem.

Where the flow detector 326 is a pressure sensor and the pump 320 is operating to deliver fluid through the branching catheter system 300, the initial sensor state is preferably equivalent to the baseline pressure (the predetermined pressure for which the branching catheter system 300 was intended to operate) as represented by the first column of the flow chart depicted in FIG. 5 and summarized as case 27 in Table I. In that state, it may be concluded that catheter flow is normal and there are no occlusions or cuts in the supply catheter 322 or the branch catheters L & R.

For instance, where the flow detector 326 is a pressure sensor and the initial sensor state is "at or near maximum," the physician may activate valve ZA2 to shunt flow though the supply catheter 322 out of the branching catheter system 300 and monitor the response of the flow detector 326 (which, as discussed above, may preferably be a pressure sensor). If the sensor reading remains at or near maximum after activation of bleeder valve ZA2, it may be concluded that an occlusion is present in the supply catheter 322 that prevents or substantially impedes flow through the supply catheter 322. However, where the activation of bleeder valve ZA2 results in a pressure reading at or near zero, then it may be concluded that there is an occlusion in both the left and right branch catheters L & R.

A more involved interrogation is illustrated by the fourth column of FIG. 5 where an initial sensor state of a flow detector 326 in the form of a pressure sensor is "at or near zero." If the physician activates supply valve ZA1 and the reading does not change, it may be concluded that there is a cut in the supply catheter 322 (or the supply catheter 322 is disconnected at either end). Yet if activation of supply valve ZA1 results in a subsequent pressure reading that is at or near maximum pressure of the pump 320, the physician may proceed to activate branch valve ZB.

If activation of branch valve ZB as depicted in the fourth column results in a third pressure reading that is "at or near zero," then branch valve ZC may be activated, whereupon the identified sensor responses and resulting catheter failures ("conclusions") may be identified as shown in FIG. 5. If, after activation of branch valve ZC, the fourth pressure reading is "twice baseline," then it may be concluded that there is a cut in the right branch catheter R. Alternatively, if activation of branch valve ZC results in a sensor reading of "at or near max" then it may be concluded that the left branch catheter L is occluded and that the right branch catheter R includes a cut (or is disconnected from the system 300). In another alternative, activation of branch valve ZC may result in a sensor reading of "at or near zero." In that situation, it may be concluded that both of the left and right branch catheters L & R are either cut or disconnected from the branching catheter system 300.

Still in the fourth column of the flow chart of FIG. 5, if the third pressure reading (after activation of branch valve ZB) is "at or near max" then it may be concluded that there is an occlusion in the right branch catheter R and a cut in the left branch catheter L (or disconnection of the left branch catheter L from the system 300). Alternatively, if activation of branch valve ZB in the fourth column of the flow chart of FIG. 5 results in a third sensor reading of "twice baseline" then it may be concluded that the left branch catheter L is either cut (or disconnected from the system 300).

It should be noted that, after activating supply valve ZA1 and noting an increase in the sensor response to "at or near maximum" (as the second sensor reading) a user could choose to activate branch valve ZC instead of branch valve ZB as the subsequent action. In this case, activating branch valve ZB would be the third user action, and the resulting conclusions depicted in column four of the flowchart could be revised to substitute "left" for "right" and vice versa.

Although flow restrictors 310 located in the branch catheters (preferably proximate the distal end or tip of the branch catheters) may facilitate robust detection of fluid flow problems using a pressure sensor and may additionally be used to control (e.g., equalize) flow through the different branch catheters, diagnostic systems in accordance with other embodiments of the present invention could be implemented without the use of such flow restrictors. Moreover, while described herein in the context of pressure sensors, it is contemplated that other flow detectors, e.g., flow sensors, could also be used.

Furthermore, if only the detection of occlusions were desirable, (i.e., no desire to detect catheter cuts or disconnections), then left and right restrictors 310 could be located anywhere downstream of the branch valves along the length of the respective left and right branch catheters L and R, rather than near the distal ends/tips of the branch catheters.

If provided, flow restrictors used in the branching catheter systems of the present invention may take any suitable form, some examples of which may be described in U.S. Patent Application Publication No. US 2004/0199128 A1 (Morris et al.), entitled CATHETER FOR TARGET SPECIFIC DRUG DELIVERY; as well as in the priority application on which the present application is based (U.S. Provisional Application No. 60/564,473, titled CATHETER SYSTEM HAVING FLOW RESTRICTION, AND DIAGNOSTIC SYSTEM FOR USE WITH SAME, filed Apr. 22, 2004); and in co-pending U.S. patent application Ser. No. 11/112,077, titled CATHETER SYSTEMS HAVING FLOW RESTRICTORS, filed on even date herewith.

As used herein and in the appended claims, the singular forms "a," "and," and "the" include plural referents unless the context clearly dictates otherwise. Thus, for example, reference to "a" or "the" component may include one or more of the components and equivalents thereof known to those skilled in the art.

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein.

The invention claimed is:

1. An implantable branched catheter system comprising:
a supply catheter section comprising a proximal end and a distal end;
two or more delivery branches in fluid communication with the distal end of the supply catheter section, wherein each delivery branch of the two or more delivery branches comprises:
a delivery catheter section comprising a proximal end and a distal end;
a flow restrictor located along the delivery catheter section, wherein the flow restrictor restricts flow through the delivery catheter section, wherein the flow restrictor is located proximate a distal end of the delivery catheter section;
a branch valve located between the distal end of the supply catheter section and the proximal end of the delivery catheter section;
a supply valve located proximate the distal end of the supply catheter section, wherein the supply valve controls flow through the distal end of the supply catheter section; and
a flow detector located proximate the proximal end of the supply catheter section, wherein the flow detector detects flow through the supply catheter section.

2. A catheter system according to claim 1, the system further comprising a bleeder valve located proximate the distal end of the supply catheter section, wherein the bleeder valve is located distal of the supply valve, and wherein the bleeder valve shunts flow out of the branched catheter system.

3. A catheter system according to claim 1, wherein the flow detector comprises a pressure sensor.

4. A catheter system according to claim 1, wherein the flow detector comprises a flow sensor.

5. A catheter system according to claim 1, further comprising a controller operatively connected to each of the supply valve, the flow detector, and the branch valve in each delivery branch of the two or more delivery branches.

6. A catheter system according to claim 1, further comprising a pump operatively connected to the proximal end of the supply catheter section.

7. A catheter system according to claim 6, wherein the flow detector comprises a pressure sensor located within the pump.

8. An implantable branched catheter system comprising:
a supply catheter section comprising a proximal end and a distal end;

two or more delivery branches in fluid communication with the distal end of the supply catheter section, wherein each delivery branch of the two or more delivery branches comprises:
  a delivery catheter section comprising a proximal end and a distal end;
  a flow restrictor located along the delivery catheter section, wherein the flow restrictor restricts flow through the delivery catheter section;
  a branch valve located between the distal end of the supply catheter section and the proximal end of the delivery catheter section;
a supply valve located proximate the distal end of the supply catheter section, wherein the supply valve controls flow through the distal end of the supply catheter section; and
a flow detector located proximate the proximal end of the supply catheter section, wherein the flow detector detects flow through the supply catheter section; and
a branched catheter connector body comprising:
  an inlet port to which the distal end of the supply catheter section is connected;
  two or more outlet ports in fluid communication with the inlet port, wherein each delivery branch of the two or more delivery branches is in fluid communication with one of the outlet ports;
  wherein the supply valve and the branch valve of each delivery branch of the two or more delivery branches are located within the connector body.

9. An implantable branched catheter system comprising:
a supply catheter section comprising a proximal end and a distal end;
two or more delivery branches in fluid communication with the distal end of the supply catheter section, wherein each delivery branch of the two or more delivery branches comprises:
  a delivery catheter section comprising a proximal end and a distal end;
  a flow restrictor located proximate a distal end of the delivery catheter section, wherein the flow restrictor restricts flow through the delivery catheter section;
  a branch valve located between the distal end of the supply catheter section and the proximal end of the delivery catheter section;
a supply valve located proximate the distal end of the supply catheter section, wherein the supply valve controls flow through the distal end of the supply catheter section;
a bleeder valve located proximate the distal end of the supply catheter section, wherein the bleeder valve is located distal of the supply valve, and wherein the bleeder valve shunts flow out of the branched catheter system; and
a flow detector located proximate the proximal end of the supply catheter section, wherein the flow detector comprises a pressure sensor.

10. A catheter system according to claim 9, further comprising a pump operatively connected to the proximal end of the supply catheter section.

11. A branching catheter connector for use in an implantable branching catheter system, the connector comprising:
an implantable connector body defining a fluid path comprising a branch point at which the fluid path separates into two or more branches;
an inlet port located within the connector body, the inlet port in fluid communication with the fluid path;
two or more outlet ports in fluid communication with the inlet port through the branching fluid path, wherein the branch point is located between the inlet port and the two or more outlet ports, and wherein the two or more outlet ports are located within the connector body;
a supply valve located proximate the inlet port, wherein the supply valve is located in the branching fluid path between the inlet port and the branch point; and
a branch valve located proximate each outlet port of the two or more outlet ports, wherein the branch valve of each outlet port is located in the fluid path between the branch point and the outlet port.

12. A branching catheter connector according to claim 11, further comprising a bleeder valve located in the fluid path between the supply valve and the branch point, and wherein the bleeder valve shunts flow out of the connector body.

13. A branching catheter connector according to claim 11, further comprising a controller operatively connected to the supply valve and the branch valves located proximate each outlet port.

14. A branching catheter connector according to claim 11, wherein the supply valve is located within the connector body.

15. A branching catheter connector according to claim 11, wherein the branch valve located proximate each outlet port of the two or more outlet ports is located within the connector body.

16. A branching catheter connector according to claim 11, wherein the two or more outlet ports and the supply valve are located within the connector body.

17. A branching catheter connector according to claim 11, wherein the two or more outlet ports and the branch valve located proximate each outlet port of the two or more outlet ports are located within the connector body.

18. A branching catheter connector according to claim 11, wherein the two or more outlet ports, the supply valve, and the branch valve located proximate each outlet port of the two or more outlet ports are located within the connector body.

19. An implantable branched catheter system comprising:
a supply catheter section comprising a proximal end and a distal end;
two or more delivery branches in fluid communication with the distal end of the supply catheter section, wherein each delivery branch of the two or more delivery branches comprises:
  a delivery catheter section comprising a proximal end and a distal end;
  a flow restrictor located along the delivery catheter section, wherein the flow restrictor restricts flow through the delivery catheter section;
  a branch valve located between the distal end of the supply catheter section and the proximal end of the delivery catheter section;
a supply valve located proximate the distal end of the supply catheter section, wherein the supply valve controls flow through the distal end of the supply catheter section;
a bleeder valve located proximate the distal end of the supply catheter section, wherein the bleeder valve is located distal of the supply valve, and wherein the bleeder valve shunts flow out of the branched catheter system; and
a flow detector located proximate the proximal end of the supply catheter section, wherein the flow detector detects flow through the supply catheter section.

20. A catheter system according to claim 19, wherein the flow detector comprises a flow sensor.

21. A catheter system according to claim 19, further comprising a controller operatively connected to each of the supply valve, the flow detector, and the branch valve in each delivery branch of the two or more delivery branches.

22. A catheter system according to claim 19, further comprising a pump operatively connected to the proximal end of the supply catheter section.

23. A catheter system according to claim 22, wherein the flow detector comprises a pressure sensor located within the pump.

24. A catheter system according to claim 19, wherein the system further comprises branched catheter connector body comprising:

an inlet port to which the distal end of the supply catheter section is connected;

two or more outlet ports in fluid communication with the inlet port, wherein each delivery branch of the two or more delivery branches is in fluid communication with one of the outlet ports;

wherein the supply valve and the branch valve of each delivery branch of the two or more delivery branches are located within the connector body.

* * * * *